United States Patent
Johnson et al.

(10) Patent No.: US 10,532,013 B2
(45) Date of Patent: *Jan. 14, 2020

(54) METHOD OF ACHIEVING IMPROVED PRODUCT RHEOLOGY, COSMETIC CONSUMER ACCEPTANCE AND DEPOSITION

(71) Applicant: The Procter & Gamble Company, Cincinnati, OH (US)

(72) Inventors: Eric Scott Johnson, Hamilton, OH (US); Sean Michael Renock, Loveland, OH (US); Mark Anthony Brown, Union, KY (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/284,930

(22) Filed: May 22, 2014

(65) Prior Publication Data

US 2014/0348886 A1 Nov. 27, 2014

Related U.S. Application Data

(60) Provisional application No. 61/826,214, filed on May 22, 2013.

(51) Int. Cl.
| | | |
|---|---|---|
| A61K 8/27 | (2006.01) | |
| A61K 8/34 | (2006.01) | |
| A61K 8/81 | (2006.01) | |
| A61K 8/86 | (2006.01) | |
| A61Q 5/00 | (2006.01) | |
| A61Q 5/02 | (2006.01) | |
| A61Q 5/12 | (2006.01) | |
| A61K 8/73 | (2006.01) | |
| A61K 8/02 | (2006.01) | |

(52) U.S. Cl.
CPC .............. *A61K 8/27* (2013.01); *A61K 8/0245* (2013.01); *A61K 8/345* (2013.01); *A61K 8/737* (2013.01); *A61K 8/8158* (2013.01); *A61K 8/86* (2013.01); *A61Q 5/00* (2013.01); *A61Q 5/02* (2013.01); *A61Q 5/12* (2013.01); *A61K 2800/28* (2013.01); *A61K 2800/412* (2013.01)

(58) Field of Classification Search
CPC ... A61Q 5/02; A61Q 5/00; A61Q 5/12; A61K 8/0245; A61K 8/27; A61K 8/737; A61K 8/86; A61K 8/8158; A61K 8/345; A61K 2800/412; A61K 2800/28
See application file for complete search history.

(56) References Cited

U.S. PATENT DOCUMENTS

| | | |
|---|---|---|
| 2,809,971 A | 10/1957 | Bernstein |
| 3,236,733 A | 2/1966 | Karsten |
| 3,753,196 A | 8/1973 | Kurtz et al. |
| 3,761,418 A | 9/1973 | Parran |
| 4,323,683 A | 4/1982 | Bolich, Jr. et al. |
| 4,345,080 A | 8/1982 | Bolich, Jr. |
| 4,379,753 A | 4/1983 | Bolich, Jr. |
| 4,470,982 A | 9/1984 | Winkler |
| 5,104,646 A | 4/1992 | Bolich, Jr. et al. |
| 5,106,609 A | 4/1992 | Bolich, Jr. et al. |
| 5,723,112 A | 3/1998 | Bowser et al. |
| 5,925,615 A | 7/1999 | Kern et al. |
| 6,102,846 A | 8/2000 | Patton et al. |
| 6,190,314 B1 | 2/2001 | Ark et al. |
| 6,293,904 B1 | 9/2001 | Blazey et al. |
| 6,306,077 B1 | 10/2001 | Prabhu et al. |
| 6,309,342 B1 | 10/2001 | Blazey et al. |
| 6,333,027 B1 * | 12/2001 | Hopkins ............... A61K 8/442 424/70.1 |
| 6,520,905 B1 | 2/2003 | Surve et al. |
| 6,572,562 B2 | 6/2003 | Marshall |
| 6,798,898 B1 | 9/2004 | Fedorovskaya et al. |
| 6,994,670 B2 | 2/2006 | Teicher et al. |
| 7,303,744 B2 | 12/2007 | Wells et al. |
| 8,349,301 B2 | 1/2013 | Wells et al. |
| 8,349,302 B2 | 1/2013 | Johnson et al. |
| 8,361,448 B2 | 1/2013 | Johnson et al. |
| 8,361,449 B2 | 1/2013 | Wells et al. |

(Continued)

FOREIGN PATENT DOCUMENTS

| | | |
|---|---|---|
| CN | 101904908 | 12/2010 |
| EP | 0074819 A2 | 3/1983 |

(Continued)

OTHER PUBLICATIONS

Imokawa et al. ("Antimicrobial effect of pyrithione" in J. Soc. Cosmet. Chem., 33, 27-37 (Jan./Feb. 1982).*
PCT International Search Report and Written Opinion for PCT/US2014/039102 dated Sep. 19, 2014.
All final and non-final office actions for U.S. Appl. No. 13/646,272.
All final and non-final office actions for U.S. Appl. No. 13/646,300.
All final and non-final office actions for U.S. Appl. No. 14/289,589.
All final and non-final office actions for U.S. Appl. No. 15/004,284.
Engmann, J. et al. "Squeeze Flow Theory and Applications to Rheometry: A Review" J. of Non-Newtonian Fluid Mechanics, 132 (2005) 1-27.

(Continued)

*Primary Examiner* — Blessing M Fubara
(74) *Attorney, Agent, or Firm* — Linda M. Sivik

(57) ABSTRACT

A method of achieving improved composition rheology, cosmetic consumer acceptance and deposition comprising applying to hair a composition comprising from about 0.01% to about 2% of a cationic polymer; from about 0.5% to 3% of an associative thickener; from about 1.0% to 10.0% of a polyol; an anti-dandruff active; a cosmetically acceptable carrier; a surfactant; wherein the composition comprises a yield consistency value of about 0.001 s to 0.9 s and having a rate index value of from about 0.01 to about 0.6 and a percentage of coacervate particles with a floc size of greater than about 20 microns is from about 1% to about 40%.

17 Claims, 1 Drawing Sheet

(56) References Cited

U.S. PATENT DOCUMENTS

| | | | |
|---|---|---|---|
| 8,361,450 B2 | 1/2013 | Johnson et al. | |
| 8,367,048 B2 | 2/2013 | Wells et al. | |
| 8,435,501 B2 | 5/2013 | Peffly et al. | |
| 8,470,305 B2 | 6/2013 | Johnson et al. | |
| 8,475,777 B2 | 7/2013 | Rautschek | |
| 8,491,877 B2 | 7/2013 | Schwartz et al. | |
| 8,524,262 B2 | 9/2013 | Roy et al. | |
| 8,560,045 B2 | 10/2013 | Burke | |
| 8,980,239 B2* | 3/2015 | Staudigel | A61Q 5/12 424/70.27 |
| 9,272,164 B2 | 3/2016 | Johnson et al. | |
| 9,427,391 B2 | 8/2016 | Peffly et al. | |
| 9,662,291 B2 | 5/2017 | Johnson et al. | |
| 2002/0077256 A1 | 6/2002 | Niemiec et al. | |
| 2002/0168327 A1 | 11/2002 | Bailey et al. | |
| 2003/0108501 A1 | 6/2003 | Hofrichter et al. | |
| 2003/0139344 A1 | 7/2003 | Hung et al. | |
| 2003/0176303 A1 | 9/2003 | Niemiec et al. | |
| 2004/0057920 A1 | 3/2004 | Focht et al. | |
| 2004/0157754 A1 | 8/2004 | Geary et al. | |
| 2004/0157755 A1 | 8/2004 | Niemiec et al. | |
| 2004/0234484 A1 | 11/2004 | Peffly et al. | |
| 2006/0134049 A1* | 6/2006 | Keenan | A61K 8/81 424/70.15 |
| 2006/0224077 A1 | 10/2006 | Pauly et al. | |
| 2006/0229505 A1 | 10/2006 | Mundt et al. | |
| 2007/0009463 A1 | 1/2007 | Niebauer et al. | |
| 2007/0207109 A1 | 9/2007 | Peffly et al. | |
| 2007/0276087 A1 | 11/2007 | Paul | |
| 2008/0091098 A1 | 4/2008 | Burke | |
| 2008/0131386 A1 | 6/2008 | Hahn et al. | |
| 2008/0206179 A1 | 8/2008 | Peffly et al. | |
| 2008/0206355 A1 | 8/2008 | Schwartz et al. | |
| 2009/0176674 A1 | 7/2009 | Peffly et al. | |
| 2010/0056430 A1* | 3/2010 | Lester | A61K 9/0014 514/1.1 |
| 2010/0249060 A1* | 9/2010 | Smith | A61K 9/0014 514/54 |
| 2011/0002868 A1 | 1/2011 | Bierganns et al. | |
| 2012/0016257 A1 | 1/2012 | Burke | |
| 2012/0164198 A1 | 6/2012 | Johnson et al. | |
| 2013/0089586 A1* | 4/2013 | Johnson | A61Q 5/12 424/401 |
| 2013/0309283 A1 | 11/2013 | Rautschek et al. | |
| 2014/0357962 A1 | 12/2014 | Harrington et al. | |
| 2016/0287509 A1 | 10/2016 | Peffly et al. | |

FOREIGN PATENT DOCUMENTS

| | | |
|---|---|---|
| EP | 0136914 A2 | 4/1985 |
| EP | 1437121 | 4/1985 |
| JP | 4918918 | 5/1974 |
| WO | WO9966886 A1 | 12/1999 |
| WO | WO2013050241 A1 | 4/2013 |

OTHER PUBLICATIONS http://rocketnews24.com/2012/11/18/266667/, "Itch is contagious just by watching others' scratching their body/nervous and more discriminating than those with negative thoughts."

Lepilleur, Carole, et al. "Use of Statistical modeling to predict the effect of formulation composition on coacervation, silicone deposition, and conditioning sensory performance of Cationic Cassia Polymers" J. Cosmet Sci., 62, 161-177.

Morioka, H. et al. "Effects of Zinc on the New Preparation Method of Hydroxy Double Salts" Inorg. Chem. 1999, 38, 4211-6.

Papoiu et al., "Contagious itch in humans: a study of visual 'transmission' of itch in atopic dermatitis and healthy subjects", Feb. 27, 2011, British Journal of Dermatology, pp. 1299-1303.

PCT International Search Report and Written Opinion for PCT/US2012/058909 dated Nov. 7, 2013.

PCT International Search Report and Written Opinion for PCT/US2012/058990 dated Nov. 7, 2013.

PCT International Search Report and Written Opinion for PCT/US2014/039706 dated Sep. 26, 2014.

* cited by examiner

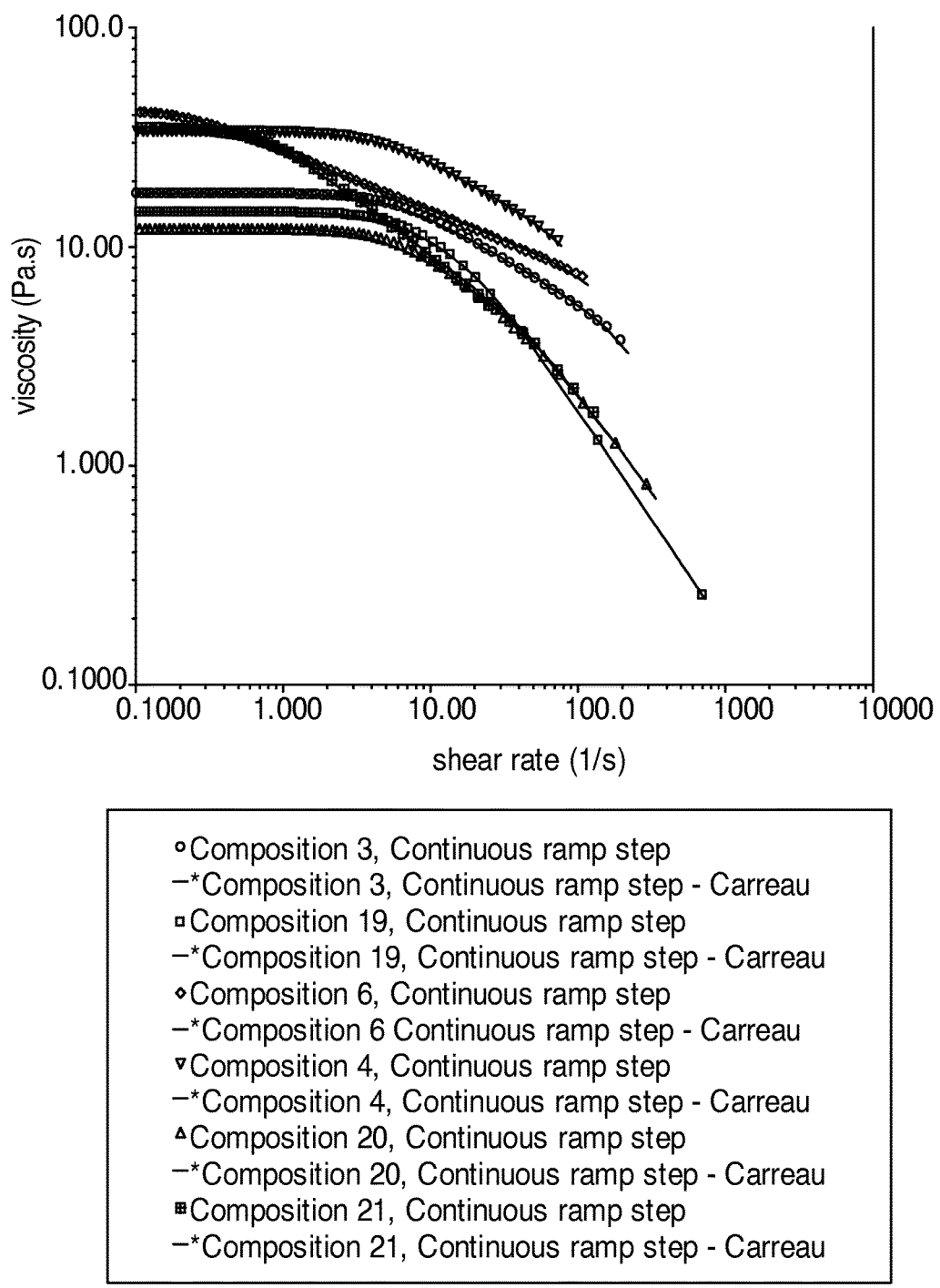

METHOD OF ACHIEVING IMPROVED PRODUCT RHEOLOGY, COSMETIC CONSUMER ACCEPTANCE AND DEPOSITION

FIELD OF THE INVENTION

A method of achieving improved shampoo rheology for a composition which translates into a consumer acceptable lather, rinsing, conditioning and manageability profile while maintaining anti-dandruff active deposition and coacervate floc size.

BACKGROUND OF THE INVENTION

Conditioning shampoos or "2 in 1" hair products comprising a detersive surfactant and hair conditioning agents are known. These personal care compositions typically comprise an anionic detersive surfactant in combination with a conditioning agent such as a silicone, hydrocarbon oil, fatty esters etc. These products have become more popular among consumers as a means of conveniently obtaining hair conditioning and cleansing performance from a single product.

Many conditioning personal care compositions, however, do not provide sufficient deposition of conditioning agents onto hair or skin during the application process and if deposition is possible, it is only possible in formulations with relatively low levels of anionic surfactant. Without adequate deposition, large proportions of conditioning agent are rinsed away during the application process and therefore provide little or no conditioning benefit. Without sufficient deposition of the conditioning agent on the hair or skin, relatively high levels of conditioning agents may be needed. Such high levels of a conditioning agent, however, can increase raw material costs, reduce lathering, and present product stability concerns. Additionally, limitations on total anionic surfactant in order to form coacervate can limit the lather potential of a composition, or result in the need for higher levels of less cost effective amphoteric surfactants in order to achieve good lather.

One known method for improving deposition of a hair conditioning agent onto hair involves the use of specific cationic deposition polymers. These polymers may be synthetic, but are most commonly natural cellulosic or guar polymers that have been modified with cationic substituents.

The formation of coacervate upon dilution of the cleansing composition with water is important to improving deposition of various conditioning actives, especially those that have small droplet sizes (i.e., ≤2 microns). In order to form coacervate, cleansing compositions comprising typical cationic polymers tend to be significantly limited in total anion concentrations, in order to achieve adequate levels of coacervate upon dilution, but this will limit the volume of lather that can be achieved with a particular cleansing composition. Thus, for cost effective, high lathering, coacervate-forming compositions, it is desirable to use a cationic polymer that can form coacervate in the presence of high levels of anionic surfactant. Another complexity arises when the composition comprises an anti-dandruff active which also needs to be deposited on the scalp in an efficacious deposition amount and quality. However, excellent deposition amount and quality of anti-dandruff actives, for example by utilizing high levels of cationic polymers and those with higher charge density, is often associated with a hair conditioning feel that many consumers find unacceptable.

Consequently, needs exist for a conditioning anti-dandruff composition that provides consumer acceptable lather, rinsing, conditioning and manageability profile while maintaining anti-dandruff active deposition and coacervate floc size.

SUMMARY OF THE INVENTION

According to a first aspect, the present invention relates to a method of achieving improved shampoo rheology which translates into consumer preferred lather creaminess and overall clean preference while maintaining increased deposition.

An embodiment of the present invention, is directed to a method of achieving improved composition rheology, cosmetic consumer acceptance and deposition comprising applying to hair a composition comprising from about 0.01% to about 2% of a cationic polymer; from about 0.5% to 3% of an associative thickener; from about 1.0% to 10.0% of a polyol; an anti-dandruff active; a cosmetically acceptable carrier; a surfactant; wherein the composition comprises a yield consistency value of about 0.001 s to 0.9 s and having a rate index value of from about 0.01 to about 0.6 and a percentage of coacervate particles with a floc size of greater than about 20 microns is from about 1% to about 40%.

BRIEF DESCRIPTION OF THE DRAWINGS

FIG. 1: Axis X; Shear rate (1/s). Axis Y. Viscosity (Pa·s). Markers represent data collection from the continuous ramp rheology experimentation collected at 30 pts per decade within the range of [log] 0.1 to 10000 shear rate (1/s). Black lines represent Carreau model data fit and measurement.

DETAILED DESCRIPTION OF THE INVENTION

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. The weight average molecular weight may be measured by gel permeation chromatography "QS" means sufficient quantity for 100%.

All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

Herein, "comprising" means that other steps and other ingredients which do not affect the end result can be added. This term encompasses the terms "consisting of" and "consisting essentially of". The compositions, methods, uses, kits, and processes of the present invention can comprise, consist of, and consist essentially of the elements and limitations of the invention described herein, as well as any of the additional or optional ingredients, components, steps, or limitations described herein.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. A polymer comprises at least two monomers. Polymers made from two or more different types of monomers are called copolymers. The distribution of the different monomers can be calculated statistically or blockwise—both possibilities are suitable for the present invention. Except if stated otherwise, the term "polymer" used herein includes any type of polymer including homopolymers and copolymers.

"Kit," as used herein, means a packaging unit comprising a plurality of components. An example of a kit is, for example, a first composition and a separately packaged second composition. Another kit may comprise a first composition and an energy delivery device. A different kit may comprise three different types of separately packaged composition and a hair styling implement. A further kit may comprise application instructions comprising a method and a composition/formulation.

The term "coacervate" as used herein, means the complex which forms between surfactant and polymer that may either be soluble or insoluble in the neat composition, typically forming an insoluble complex in the neat composition, and which may become less soluble upon dilution and thus yielding an increase in its level of phase separation or precipitate in solution.

The term "charge density" as used herein, means the ratio of the number of positive charges on a monomeric unit (of which a polymer is comprised) to the M.Wt. of said monomeric unit. The charge density multiplied by the polymer M.Wt. determines the number of positively charged sites on a given polymer chain. For cationic guars, charge density is measured using standard elemental analysis of percentage nitrogen known to one skilled in the art. This value of percentage nitrogen, corrected for total protein analysis, can then be used to calculate the number or equivalence of positive charges per gram of polymer. For the cationic copolymers, the charge density is a function of the monomers used in the synthesis. Standard NMR techniques know to one skilled in the art would be used to confirm that ratio of cationic and non-ionic monomers in the polymer. This would then be used to calculate the number or equivalence of positive charger per gram of polymer. Once these values are know, the charge density is reported in milliequivalence (meq) per gram of cationic polymer.

The term "(meth)acrylamide" as used herein means methylacrylamide or acrylamide. The term "(meth)acrylic acid" as used herein means acrylic acid or methacrylic acid.

It has been surprisingly found that, by formulating specific levels of an associative thickener and a polyol with cationic polymer that non Antidandruff cosmetic consumers perceive increased lather, conditioning and manageability through modifying the shampoos rheological profile. This enhances the cosmetic qualities of an anti-dandruff shampoo thereby making its properties much more enjoyable to use. This will encourage consumers who would not normally want to use an anti-dandruff shampoo because of its aesthetic profile to be compliant with product use. It has been shown that with these enhanced rheological properties and by controlling the coacervate floc size that a cosmetically acceptable and efficacious anti-dandruff product can be achieved for this consumer.

Without being bound by theory, the present invention has found to have the features of the method according to the first aspect, as well as the other aspects and other relevant components, are described in detail hereinafter. All components of the composition described herein should be physically and chemically compatible with the essential components described herein, and should not otherwise unduly impair product stability, aesthetics or performance.

Deposition Polymer

The shampoo composition also comprises a cationic deposition polymer. These cationic deposition polymers can include at least one of (a) a cationic guar polymer, (b) a cationic non-guar galactomannan polymer, (c) a cationic tapioca polymer, (d) a cationic copolymer of acrylamide monomers and cationic monomers, and/or (e) a synthetic, non-crosslinked, cationic polymer, which may or may not form lyotropic liquid crystals upon combination with the detersive surfactant (f) a cationic cellulose polymer. Additionally, the cationic deposition polymer can be a mixture of deposition polymers.

(1) Cationic Guar Polymers

According to an embodiment of the present invention, the shampoo composition comprises a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of $\beta(1\text{-}4)$ glycosidic linkages. The galactose branching arises by way of an $\alpha(1\text{-}6)$ linkage. Cationic derivatives of the guar gums are obtained by reaction between the hydroxyl groups of the polygalactomannan and reactive quaternary ammonium compounds. The degree of substitution of the cationic groups onto the guar structure must be sufficient to provide the requisite cationic charge density described above.

According to one embodiment, the cationic guar polymer has a weight average M.Wt. of less than about 2.5 million g/mol, and has a charge density of from about 0.05 meq/g to about 2.5 meq/g. In an embodiment, the cationic guar polymer has a weight average M.Wt. of less than 1.5 million g/mol, or from about 150 thousand to about 1.5 million g/mol, or from about 200 thousand to about 1.5 million g/mol, or from about 300 thousand to about 1.5 million g/mol, or from about 700,000 thousand to about 1.5 million g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.7 meq/g.

According to one embodiment, the cationic guar polymer has a weight average M.Wt. of less than about 1 million g/mol, and has a charge density of from about 0.1 meq/g to about 2.5 meq/g. In an embodiment, the cationic guar polymer has a weight average M.Wt. of less than 900 thousand g/mol, or from about 150 thousand to about 800 thousand g/mol, or from about 200 thousand to about 700 thousand g/mol, or from about 300 thousand to about 700 thousand g/mol, or from about 400 thousand to about 600 thousand g/mol. from about 150 thousand to about 800 thousand g/mol, or from about 200 thousand to about 700 thousand g/mol, or from about 300 thousand to about 700 thousand g/mol, or from about 400 thousand to about 600 thousand g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.5 meq/g.

In an embodiment, the composition comprises from about 0.01% to less than about 0.7%, or from about 0.04% to about 0.55%, or from about 0.08% to about 0.5%, or from about 0.16% to about 0.5%, or from about 0.2% to about 0.5%, or from about 0.3% to about 0.5%, or from about 0.4% to about 0.5%, of cationic guar polymer (a), by total weight of the composition.

The cationic guar polymer may be formed from quaternary ammonium compounds. In an embodiment, the quaternary ammonium compounds for forming the cationic guar polymer conform to the general formula 1:

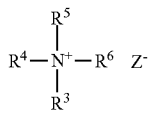

wherein where $R^3$, $R^4$ and $R^5$ are methyl or ethyl groups; $R^6$ is either an epoxyalkyl group of the general formula 2:

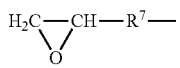

or $R^6$ is a halohydrin group of the general formula 3:

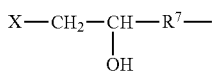

wherein $R^7$ is a $C_1$ to $C_3$ alkylene; X is chlorine or bromine, and Z is an anion such as Cl—, Br—, I— or $HSO_4$—.

In an embodiment, the cationic guar polymer conforms to the general formula 4:

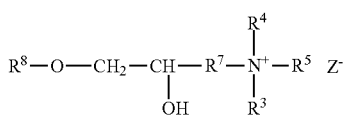

wherein $R^8$ is guar gum; and wherein $R^4$, $R^5$, $R^6$ and $R^7$ are as defined above; and wherein Z is a halogen. In an embodiment, the cationic guar polymer conforms to Formula 5:

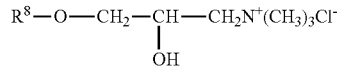

Suitable cationic guar polymers include cationic guar gum derivatives, such as guar hydroxypropyltrimonium chloride. In an embodiment, the cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a M.Wt. of 500,000 g/mole. Jaguar® C-17, which has a cationic charge density of about 0.6 meq/g and a M.Wt. of about 2.2 million g/mol and is available from Rhodia Company. Jaguar® C 13S which has a M.Wt. of 2.2 million g/mol and a cationic charge density of about 0.8 meq/g (available from Rhodia Company). Other suitable guar hydroxypropyltrimonium chloride are: guar hydroxypropyltrimonium chloride which has a charge density of about 1.1 meq/g and a M.Wt. of about 500,000 g/mole is available from ASI, a charge density of about 1.5 meq/g and a M.Wt. of about 500,000 g/mole is available from ASI.

Other suitable guar hydroxypropyltrimonium chloride are: Hi-Care 1000, which has a charge density of about 0.7 meq/g and a M.Wt. of about 600,000 g/mole and is available from Rhodia; N-Hance 3269 and N-Hance 3270, which has a charge density of about 0.7 meq/g and a M.Wt. of about 425,000 g/mole and is available from ASI; N-Hance 3196, which has a charge density of about 0.8 and a M. Wt. Of about 1,100,000 g/mole and is available from ASI. AquaCat CG518 has a charge density of about 0.9 meq/g and a M.Wt. of about 50,000 g/mole is available from ASI. BF-13, which is a borate (boron) free guar of charge density of about 1.1 meq/g and M. W.t of about 800,000 and BF-17, which is a borate (boron) free guar of charge density of about 1.7 meq/g and M. W.t of about 800,000 both available from ASI.

(2) Cationic Non-Guar Galactomannan Polymers

The shampoo compositions of the present invention comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β(1-4) glycosidic linkages. The galactose branching arises by way of an α(1-6) linkage. The ratio of mannose monomers to galactose monomers varies according to the species of the plant and also is affected by climate. Non Guar Galactomannan polymer derivatives of the present invention have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and Cassia gum (5 parts mannose/1 part galactose).

In one embodiment of the invention, the non-guar galactomannan polymer derivatives have a M. Wt. from about 1,000 to about 10,000,000, and/or form about 5,000 to about 3,000,000.

The shampoo compositions of the present invention include galactomannan polymer derivatives which have a cationic charge density from about 0.5 meq/g to about 7 meq/g. In one embodiment of the present invention, the galactomannan polymer derivatives have a cationic charge density from about 1 meq/g to about 5 meq/g. The degree of substitution of the cationic groups onto the galactomannan structure should be sufficient to provide the requisite cationic charge density.

In one embodiment of the present invention, the galactomannan polymer derivative is a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

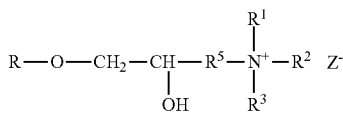

wherein R is the gum. The cationic galactomannan derivative can be a gum hydroxypropyltrimethylammonium chloride, which can be more specifically represented by the general formula 7:

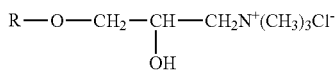

In another embodiment of the invention, the galactomannan polymer derivative is an amphoteric galactomannan polymer derivative having a net positive charge, obtained when the cationic galactomannan polymer derivative further comprises an anionic group.

In one embodiment of the invention the cationic non-guar galactomannan has a ratio of mannose to galactose is greater than about 4:1, a M.Wt. of about 100,000 to about 500,000, and/or from about 150,000 to about 400,000 and a cationic charge density from about 1 meq/g to about 5 meq/g, and/or from 2 meq/g to about 4 meq/g and is a derived from a cassia plant.

The shampoo compositions of the present invention comprise at least about 0.05% of a galactomannan polymer derivative by weight of the composition. In one embodiment of the present invention, the shampoo compositions comprise from about 0.05% to about 2%, by weight of the composition, of a galactomannan polymer derivative.

(3) Cationically Modified Starch Polymer

The shampoo compositions of the present invention comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The shampoo compositions of the present invention comprise cationically modified starch polymers at a range of about 0.01% to about 10%, and/or from about 0.05% to about 5%, by weight of the composition.

The cationically modified starch polymers disclosed herein have a percent of bound nitrogen of from about 0.5% to about 4%.

The cationically modified starch polymers for use in the shampoo compositions of the present invention have a molecular weight from about 850,000 to about 15,000,000 and/or from about 900,000 to about 5,000,000. As used herein, the term "molecular weight" refers to the weight average molecular weight. The weight average molecular weight may be measured by gel permeation chromatography ("GPC") using a Waters 600E HPLC pump and Waters 717 auto-sampler equipped with a Polymer Laboratories PL Gel MIXED-A GPC column (Part Number 1110-6200, 600.times.7.5 mm, 20 um) at a column temperature of 55.degree. C. and at a flow rate of 1.0 ml/min (mobile phase consisting of Dimethylsulfoxide with 0.1% Lithium Bromide), and using a Wyatt DAWN EOS MALLS (multi-angle laser light scattering detector) and Wyatt Optilab DSP (interferometric refractometer) detectors arranged in series (using a dn/dc of 0.066), all at detector temperatures of 50° C., with a method created by using a Polymer Laboratories narrow dispersed Polysaccharide standard (Mw=47,300), with an injection volume of 200 μl.

The shampoo compositions of the present invention include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers of the present invention generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof.

In one embodiment of the present invention, cationically modified starch polymers are selected from degraded cationic maize starch, cationic tapioca, cationic potato starch, and mixtures thereof. In another embodiment, cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers in the present invention may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance.gtoreq.80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in compositions of the present invention is available from known starch suppliers. Also suitable for use in the present invention is nonionic modified starch that could be further derivatized to a cationically modified starch as is known in the art. Other suitable modified starch starting materials may be quaternized, as is known in the art, to produce the cationically modified starch polymer suitable for use in the invention.

Starch Degradation Procedure: In one embodiment of the present invention, a starch slurry is prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

(4) Cationic Copolymer of an Acrylamide Monomer and a Cationic Monomer

According to an embodiment of the present invention, the shampoo composition comprises a cationic copolymer of an acrylamide monomer and a cationic monomer, wherein the copolymer has a charge density of from about 1.0 meq/g to about 3.0 meq/g. In an embodiment, the cationic copolymer is a synthetic cationic copolymer of acrylamide monomers and cationic monomers.

In an embodiment, the cationic copolymer comprises:
(i) an acrylamide monomer of the following Formula AM:

Formula AM

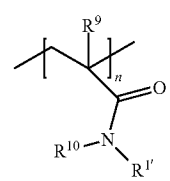

where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$ cycloalkyl; and
(ii) a cationic monomer conforming to Formula CM:

Formula CM

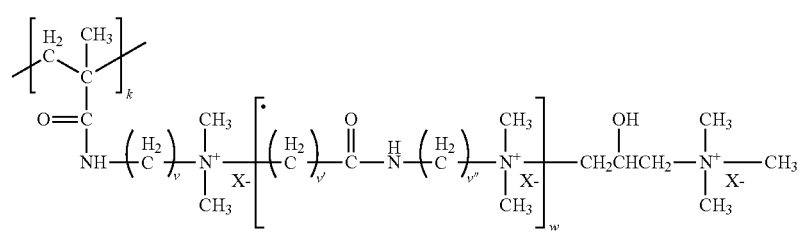

where k=1, each of v, v', and v" is independently an integer of from 1 to 6, w is zero or an integer of from 1 to 10, and $X^-$ is an anion.

In an embodiment, cationic monomer conforming to Formula CM and where k=1, v=3 and w=0, z=1 and $X^-$ is $Cl^-$ to form the following structure:

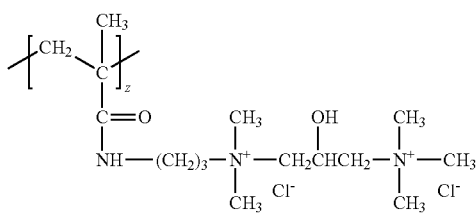

The above structure may be referred to as diquat. In another embodiment, the cationic monomer conforms to Formula CM and wherein v and v" are each 3, v'=1, w=1, y=1 and $X^-$ is $Cl^-$, such as:

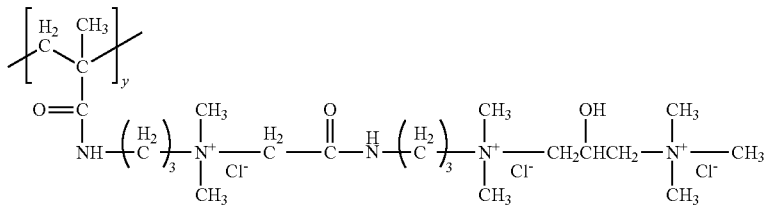

The above structure may be referred to as triquat.

In an embodiment, the acrylamide monomer is either acrylamide or methacrylamide.

In an embodiment, the cationic copolymer (b) is AM:TRIQUAT which is a copolymer of acrylamide and 1,3-Propanediaminium,N-[2-[[[dimethyl[3-[(2-methyl-1-oxo-2-propenyl)amino]propyl]ammonio]acetyl]amino]ethyl]2-hydroxy-N,N,N',N',N'-pentamethyl-, trichloride. AM:TRIQUAT is also known as polyquaternium 76 (PQ76). AM:TRIQUAT may have a charge density of 1.6 meq/g and a M.Wt. of 1.1 million g/mol.

In an alternative embodiment, the cationic copolymer is of an acrylamide monomer and a cationic monomer, wherein the cationic monomer is selected from the group consisting of: dimethylaminoethyl(meth)acrylate, dimethylaminopropyl(meth)acrylate, ditertiobutylaminoethyl(meth)acrylate, dimethylaminomethyl(meth)acrylamide, dimethylaminopropyl(meth)acrylamide; ethylenimine, vinylamine, 2-vinylpyridine, 4-vinylpyridine; trimethylammonium ethyl (meth)acrylate chloride, trimethylammonium ethyl(meth)acrylate methyl sulphate, dimethylammonium ethyl(meth)acrylate benzyl chloride, 4-benzoylbenzyl dimethylammonium ethyl acrylate chloride, trimethyl ammonium ethyl(meth)acrylamido chloride, trimethyl ammonium propyl(meth)acrylamido chloride, vinylbenzyl trimethyl ammonium chloride, diallyldimethyl ammonium chloride, and mixtures thereof.

In an embodiment, the cationic copolymer comprises a cationic monomer selected from the group consisting of: cationic monomers include trimethylammonium ethyl (meth)acrylate chloride, trimethylammonium ethyl(meth)acrylate methyl sulphate, dimethylammonium ethyl(meth)acrylate benzyl chloride, 4-benzoylbenzyl dimethylammonium ethyl acrylate chloride, trimethyl ammonium ethyl(meth)acrylamido chloride, trimethyl ammonium propyl(meth)acrylamido chloride, vinylbenzyl trimethyl ammonium chloride, and mixtures thereof.

In an embodiment, the cationic copolymer is water-soluble. In an embodiment, the cationic copolymer is formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. In an embodiment, cationized esters of the (meth)acrylic acid containing a quaternized N atom are quaternized dialkylaminoalkyl(meth)acrylates with C1 to C3 in the alkyl and alkylene groups. In an embodiment, the cationized esters of the (meth)acrylic acid containing a quaternized N atom are selected from the group consisting of: ammonium salts of dimethylaminomethyl(meth)acrylate, dimethylaminoethyl (meth)acrylate, dimethylaminopropyl(meth)acrylate, diethylaminomethyl(meth)acrylate, diethylaminoethyl(meth) acrylate; and diethylaminopropyl(meth)acrylate quaternized with methyl chloride. In an embodiment, the cationized esters of the (meth)acrylic acid containing a quaternized N atom is dimethylaminoethyl acrylate, which is quaternized with an alkyl halide, or with methyl chloride or benzyl chloride or dimethyl sulfate (ADAME-Quat). In an embodiment, the cationic monomer when based on (meth)acrylamides are quaternized dialkylaminoalkyl(meth)acrylamides with C1 to C3 in the alkyl and alkylene groups, or dimethylaminopropylacrylamide, which is quaternized with an alkyl halide, or methyl chloride or benzyl chloride or dimethyl sulfate.

In an embodiment, the cationic monomer based on a (meth)acrylamide is a quaternized dialkylaminoalkyl(meth) acrylamide with C1 to C3 in the alkyl and alkylene groups. In an embodiment, the cationic monomer based on a (meth)acrylamide is dimethylaminopropylacrylamide, which is quaternized with an alkyl halide, especially methyl chloride or benzyl chloride or dimethyl sulfate.

In an embodiment, the cationic monomer is a hydrolysis-stable cationic monomer. Hydrolysis-stable cationic monomers can be, in addition to a dialkylaminoalkyl(meth)acrylamide, all monomers that can be regarded as stable to the OECD hydrolysis test. In an embodiment, the cationic monomer is hydrolysis-stable and the hydrolysis-stable cationic monomer is selected from the group consisting of: diallyldimethylammonium chloride and water-soluble, cationic styrene derivatives.

In an embodiment, the cationic copolymer is a terpolymer of acrylamide, 2-dimethylammoniumethyl(meth)acrylate quaternized with methyl chloride (ADAME-Q) and 3-dimethylammoniumpropyl(meth)acrylamide quaternized with methyl chloride (DIMAPA-Q). In an embodiment, the cationic copolymer is formed from acrylamide and acrylamidopropyltrimethylammonium chloride, wherein the acrylamidopropyltrimethylammonium chloride has a charge density of from about 1.0 meq/g to about 3.0 meq/g.

In an embodiment, the cationic copolymer has a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

In an embodiment, the cationic copolymer has a M.Wt. from about 100 thousand g/mol to about 2 million g/mol, or from about 300 thousand g/mol to about 1.8 million g/mol, or from about 500 thousand g/mol to about 1.6 million g/mol, or from about 700 thousand g/mol to about 1.4 million g/mol, or from about 900 thousand g/mol to about 1.2 million g/mol.

In an embodiment, the cationic copolymer is a trimethylammoniopropylmethacrylamide chloride-N-Acrylamide copolymer, which is also known as AM:MAPTAC. AM:MAPTAC may have a charge density of about 1.3 meq/g and a M.Wt. of about 1.1 million g/mol. In an embodiment, the cationic copolymer is AM:ATPAC. AM:ATPAC may have a charge density of about 1.8 meq/g and a M.Wt. of about 1.1 million g/mol.

(5) Cationic Synthetic Polymer

According to an embodiment of the present invention, the shampoo composition comprises a cationic synthetic polymer that may be formed from i) one or more cationic monomer units, and optionally ii) one or more monomer units bearing a negative charge, and/or iii) a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers In one embodiment, the cationic polymers are water soluble or dispersible, non-crosslinked, and synthetic cationic polymers having the following structure:

where A, may be one or more of the following cationic moieties:

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl arylox;
where Z=C1-C22 alkyl, alkyloxy, aryl or aryloxy;
where R1=H, C1-C4 linear or branched alkyl;
where s=0 or 1, n=0 or ≥1;
where T and R7=C1-C22 alkyl; and
where X−=halogen, hydroxide, alkoxide, sulfate or alkylsulfate.

Where the monomer bearing a negative charge is defined by R2'=H, C1-C4 linear or branched alkyl and R3 as:

where D=O, N, or S;
where Q=$NH_2$ or O;
where u=1-6;
where t=0-1; and
where J=oxygenated functional group containing the following elements P, S, C.

Where the nonionic monomer is defined by R2"=H, C1-C4 linear or branched alkyl, R6=linear or branched alkyl, alkyl aryl, aryl oxy, alkyloxy, alkylaryl oxy and β is defined as $[C=G']_L$;
|
G"

and
where G' and G" are, independently of one another, O, S or N—H and L=0 or 1.

Examples of cationic monomers include aminoalkyl (meth)acrylates, (meth)aminoalkyl(meth)acrylamides;

monomers comprising at least one secondary, tertiary or quaternary amine function, or a heterocyclic group containing a nitrogen atom, vinylamine or ethylenimine; diallyl-dialkyl ammonium salts; their mixtures, their salts, and macromonomers deriving from therefrom.

Further examples of cationic monomers include dimethylaminoethyl(meth)acrylate, dimethylaminopropyl(meth)acrylate, ditertiobutylaminoethyl(meth)acrylate, dimethylaminomethyl(meth)acrylamide, dimethylaminopropyl(meth)acrylamide, ethylenimine, vinylamine, 2-vinylpyridine, 4-vinylpyridine, trimethylammonium ethyl (meth)acrylate chloride, trimethylammonium ethyl(meth)acrylate methyl sulphate, dimethylammonium ethyl(meth)acrylate benzyl chloride, 4-benzoylbenzyl dimethylammonium ethyl acrylate chloride, trimethyl ammonium ethyl(meth)acrylamido chloride, trimethyl ammonium propyl(meth)acrylamido chloride, vinylbenzyl trimethyl ammonium chloride, diallyldimethyl ammonium chloride.

Suitable cationic monomers include those which comprise a quaternary ammonium group of formula —$NR_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl(meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl(meth)acrylamido chloride, trimethyl ammonium propyl(meth)acrylamido chloride, vinylbenzyl trimethyl ammonium chloride.

Additional suitable cationic monomers include trimethyl ammonium propyl(meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide(meth)acrylate (i.e. polyethoxylated(meth) acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X–) in association with the synthetic cationic polymers may be any known counterion so long as the polymers remain soluble or dispersible in water, in the shampoo composition, or in a coacervate phase of the shampoo composition, and so long as the counterions are physically and chemically compatible with the essential components of the shampoo composition or do not otherwise unduly impair product performance, stability or aesthetics. Non limiting examples of such counterions include halides (e.g., chlorine, fluorine, bromine, iodine), sulfate and methylsulfate.

In one embodiment, the cationic polymer described herein aids in providing damaged hair, particularly chemically treated hair, with a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer returns the hair to a generally virgin-like, healthier state. Lyotropic liquid crystals are formed by combining the synthetic cationic polymers described herein with the aforementioned anionic detersive surfactant component of the shampoo composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in WO 94/06403 to Reich et al. The synthetic polymers described herein can be formulated in a stable shampoo composition that provides improved conditioning performance, with respect to damaged hair.

Cationic synthetic polymers that can form lyotropic liquid crystals have a cationic charge density of from about 2 meq/gm to about 7 meq/gm, and/or from about 3 meq/gm to about 7 meq/gm, and/or from about 4 meq/gm to about 7 meq/gm. In some embodiments, the cationic charge density is about 6.2 meq/gm. The polymers also have a M. Wt. of from about 1,000 to about 5,000,000, and/or from about 10,000 to about 2,000,000, and/or from about 100,000 to about 2,000,000.

In another embodiment of the invention cationic synthetic polymers that provide enhanced conditioning and deposition of benefit agents but do not necessarily form lytropic liquid crystals have a cationic charge density of from about 0.7 meq/gm to about 7 meq/gm, and/or from about 0.8 meq/gm to about 5 meq/gm, and/or from about 1.0 meq/gm to about 3 meq/gm. The polymers also have a M. Wt. of from about 1,000 to about 5,000,000, from about 10,000 to about 2,000,000, and from about 100,000 to about 2,000,000.

The concentration of the cationic polymers ranges about 0.025% to about 5%, from about 0.1% to about 3%, and/or from about 0.2% to about 1%, by weight of the shampoo composition.

(6) Cationic Cellulose Polymers

Suitable cationic cellulose polymers are salts of hydroxyethyl cellulose reacted with trimethyl ammonium substituted epoxide, referred to in the industry (CTFA) as Polyquaternium 10 and available from Dwo/Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

In an embodiment, the shampoo composition comprises a plurality of cationic conditioning polymers. According to one embodiment, where two cationic conditioning polymers are present, the weight ratio of a first cationic conditioning polymer to a second cationic conditioning polymer is from about 1000:1 to about 2:1. In an embodiment, the weight ratio of the first cationic conditioning polymer to the second cationic conditioning polymer is from about 1000:1 to about 4:1. In an embodiment, weight ratio of the first cationic conditioning polymer to the second cationic conditioning polymer is from about 800:1 to about 4:1, or from about 500:1 to about 4:1, or from about 100:1 to about 5:1, or from about 100:1 to about 6:1, or from about 50:1 to about 6.5:1, or from about 50:1 to about 7:1, or from about 50:1 to about 8.3:1, or from about 50:1 to about 16.7:1

The pH of the composition may be from about pH 3 to about pH 9, or from about pH 4 to about pH 7.

The composition comprises an anti-dandruff active, which may be an anti-dandruff active particulate. In an embodiment, the anti-dandruff active is selected from the group consisting of: pyridinethione salts; zinc carbonate; azoles, such as ketoconazole, econazole, and elubiol; selenium sulphide; particulate sulfur; keratolytic agents such as salicylic acid; and mixtures thereof. In an embodiment, the anti-dandruff particulate is a pyridinethione salt. Such anti-dandruff particulate should be physically and chemically compatible with the components of the composition, and should not otherwise unduly impair product stability, aesthetics or performance.

Pyridinethione particulates are suitable particulate anti-dandruff actives for use in composition of the present invention. In an embodiment, the anti-dandruff active is a 1-hydroxy-2-pyridinethione salt and is in particulate form. In an embodiment, the concentration of pyridinethione anti-dandruff particulate ranges from about 0.01% to about 5%, by weight of the composition, or from about 0.1% to about 3%, or from about 0.1% to about 2%. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"; zinc pyrithione), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. Nos. 2,809,971; 3,236,733; 3,753,196; 3,761,418; 4,345,080; 4,323,683; 4,379,753; and 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. In an embodiment, the azole anti-microbial active is ketoconazole. In an embodiment, the sole anti-microbial active is ketoconazole.

The present invention may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the composition comprises an effective amount of a zinc-containing layered material. In an embodiment, the composition comprises from about 0.001% to about 10%, or from about 0.01% to about 7%, or from about 0.1% to about 5% of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975) Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_{x}(OH)_2]^{x+}A^{m-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1-x}M^{2+}_{1+x}(OH)_{3(1-y)}]^{+}A^{n-}_{(1=3y)/n} \cdot nH_2O$ where the two metal ions ($M^{2+}$) may be the same or different. If they are the same and represented by zinc, the formula simplifies to $[Zn_{1+x}(OH)_2]^{2x+}2x\ A^{-} \cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In an embodiment, the composition comprises basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

The on-scalp deposition of the anti-dandruff active is at least about 1 microgram/cm². The on-scalp deposition of the anti-dandruff active is important in view of ensuring that the anti-dandruff active reaches the scalp where it is able to perform its function. In an embodiment, the deposition of the anti-dandruff active on the scalp is at least about 1.5 microgram/cm², or at least about 2.5 microgram/cm², or at least about 3 microgram/cm², or at least about 4 microgram/cm², or at least about 6 microgram/cm², or at least about 7 microgram/cm², or at least about 8 microgram/cm², or at least about 8 microgram/cm², or at least about 10 microgram/cm². The on-scalp deposition of the anti-dandruff active is measured by having the hair of individuals washed with a composition comprising an anti-dandruff active, for example a composition pursuant to the present invention, by trained a cosmetician according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

The composition comprises a cosmetically acceptable carrier. In an embodiment, the carrier is an aqueous carrier. The amount and chemistry of the carrier is selected according to the compatibility with other components and other desired characteristic of the product. In an embodiment, the carrier is selected from the group consisting of: water and water solutions of lower alkyl alcohols. In an embodiment, the carrier is a lower alkyl alcohol, wherein the monohydric alcohol has 1 to 6 carbons. In an embodiment, the carrier is ethanol and/or isopropanol. In an embodiment, the cosmetically acceptable carrier is a cosmetically acceptable aqueous carrier and is present at a level of from about 20% to about 95%, or from about 60% to about 85%.

The composition comprises a surfactant. The surfactant is included to provide cleaning performance to the composition. In an embodiment, the surfactant is selected from the group consisting of: anionic surfactants, amphoteric surfactants, zwitterionic surfactants, cationic surfactants, nonionic surfactants, and mixtures thereof. In an embodiment, the surfactant is an anionic surfactant. In an embodiment, the composition comprises from about 5% to about 50%, or from about 8% to about 30%, or from about 10% to about 25% of a surfactant, by total weight of the composition.

The composition may comprise a detersive surfactant system. The detersive surfactant system may comprise at least one anionic surfactant, and optionally a co-surfactant selected from the group consisting of: an amphoteric surfactant, a zwitterionic surfactant, a cationic surfactant, a nonionic surfactant, or a mixture thereof. The concentration of the detersive surfactant system in the composition should be sufficient to provide the desired cleaning and lather performance. In an embodiment, the composition comprises from about 5% to about 50%, or from about 8% to about 30%, or from about 10% to about 25% of detersive surfactant system, by total weight of the composition.

In considering the performance characteristics, such as coacervate formation, wet conditioning performance, dry conditioning performance, and conditioning agent deposition on hair, it is desirable to optimize the levels and types of surfactants in order to maximize the performance potential of polymer systems. In one embodiment, the detersive surfactant system for use in the composition comprises an anionic surfactant with an ethoxylate level and an anion level, wherein the ethoxylate level is from about 1 to about 10, and wherein the anion level is from about 1 to about 10. The combination of such an anionic surfactant with the cationic copolymer and cationic guar polymer provides enhanced deposition of conditioning agents to hair and/or skin without reducing cleansing or lathering performance.

An optimal ethoxylate level is calculated based on the stoichiometry of the surfactant structure, which in turn is based on a particular M.Wt. of the surfactant where the number of moles of ethoxylation is known. Likewise, given a specific M.Wt. of a surfactant and an anionization reaction completion measurement, the anion level can be calculated.

In an embodiment, the detersive surfactant system comprises at least one anionic surfactant comprising an anion selected from the group consisting of sulfates, sulfonates, sulfosuccinates, isethionates, carboxylates, phosphates, and phosphonates. In an embodiment, the anion is a sulfate.

In an embodiment, the anionic surfactant is an alkyl sulfate or an alkyl ether sulfate. These materials have the respective formulae $R^9OSO_3M$ and $R^9O(C_2H_4O)_xSO_3M$, wherein $R^9$ is alkyl or alkenyl of from about 8 to about 18 carbon atoms, x is an integer having a value of from about 1 to about 10, and M is a cation such as ammonium, an alkanolamine such as triethanolamine, a monovalent metal cation such as sodium and potassium, or a polyvalent metal cation such as magnesium and calcium. Solubility of the surfactant will depend upon the particular anionic surfactants and cations chosen. In an embodiment, $R^9$ has from about 8 to about 18 carbon atoms, or from about 10 to about 16 carbon atoms, or from about 12 to about 14 carbon atoms, in both the alkyl sulfates and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. In an embodiment, the alcohols are lauryl alcohol and straight chain alcohols derived from coconut oil or palm kernel oil. Such alcohols are reacted with from about 0 to about 10, or from about 2 to about 5, or about 3, molar proportions of ethylene oxide, and the resulting mixture of molecular species having, for example, an average of 3 moles of ethylene oxide per mole of alcohol is sulfated and neutralized. In an embodiment, the alkyl ether sulphate is selected from the group consisting of: sodium and ammonium salts of coconut alkyl triethylene glycol ether sulfate, tallow alkyl triethylene glycol ether sulfate, tallow alkyl hexa-oxyethylene sulphate, and mixtures thereof. In an embodiment, the alkyl ether sulfate comprises a mixture of individual compounds, wherein the compounds in the mixture have an average alkyl chain length of from about 10 to about 16 carbon atoms and an average degree of ethoxylation of from about 1 to about 4 moles of ethylene oxide. Such a mixture also comprises from about 0% to about 20% $C_{12-13}$ compounds; from about 60% to about 100% of $C_{14-15-16}$ compounds; from about 0% to about 20% by weight of $C_{17-18-19}$ compounds; from about 3% to about 30% by weight of compounds having a degree of ethoxylation of 0; from about 45% to about 90% by weight of compounds having a degree of ethoxylation from about 1 to about 4; from about 10% to about 25% by weight of compounds having a degree of ethoxylation from about 4 to about 8; and from about 0.1% to about 15% by weight of compounds having a degree of ethoxylation greater than about 8.

In an embodiment, the anionic surfactant is selected from the group consisting of: ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, and mixtures thereof. In addition to the sulfates, isethionates, sulfonates, sulfosuccinates described above, other potential anions for the anionic surfactant include phosphonates, phosphates, and carboxylates.

The composition and/or the detersive surfactant system may comprise a co-surfactant selected from the group consisting of: amphoteric surfactants, zwitterionic surfactants, cationic surfactants, non-ionic surfactants, and mixtures thereof. The concentration of such co-surfactants may be from about 0.5% to about 20%, or from about 1% to about 10%, by total weight of the composition. In an embodiment, the composition comprises a co-surfactant selected from the group consisting of: amphoteric surfactants, zwitterionic surfactants, and mixtures thereof. Non limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Amphoteric surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. In an embodiment, the amphoteric surfactant is selected from the group consisting of: sodium cocaminopropionate, sodium cocaminodipropionate, sodium cocoamphoacetate, sodium cocoamphohydroxypropylsulfonate, sodium cocoamphopropionate, sodium cornamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium cornamphopropionate, ammonium lauraminopropionate, ammonium lauroamphoacetate, ammonium lauroamphohydroxypropylsulfonate, ammonium lauroamphopropionate, ammonium cornamphopropionate, ammonium lauriminodipropionate, triethanonlamine cocaminopropionate, triethanonlamine cocaminodipropionate, triethanonlamine cocoamphoacetate, triethanonlamine cocoamphohydroxypropylsulfonate, triethanonlamine cocoamphopropionate, triethanonlamine cornamphopropionate, triethanonlamine lauraminopropionate, triethanonlamine lauroamphoacetate, triethanonlamine lauroamphohydroxypropylsulfonate, triethanonlamine lauroamphopropionate, triethanonlamine cornamphopropionate, triethanonlamine lauriminodipropionate, cocoamphodipropionic acid, disodium caproamphodiacetate, disodium caproamphoadipropionate, disodium capryloamphodiacetate, disodium capryloamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and mixtures thereof.

In one embodiment, the amphoteric surfactant is a surfactant according to the following structure:

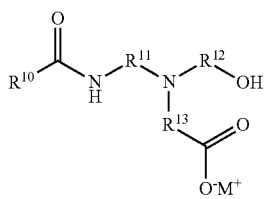

wherein $R^{10}$ is a C-linked monovalent substituent selected from the group consisting of: substituted alkyl systems comprising 9 to 15 carbon atoms, unsubstituted alkyl systems comprising 9 to 15 carbon atoms, straight alkyl systems comprising 9 to 15 carbon atoms, branched alkyl systems comprising 9 to 15 carbon atoms, and unsaturated alkyl systems comprising 9 to 15 carbon atoms; and wherein $R^{11}$, $R^{12}$, and $R^{13}$ are each independently selected from the group consisting of: C-linked divalent straight alkyl systems comprising 1 to 3 carbon atoms, and C-linked divalent branched alkyl systems comprising 1 to 3 carbon atoms; and wherein $M^+$ is a monovalent counterion selected from the group consisting of sodium, ammonium and protonated triethanolamine. In an embodiment, the amphoteric surfactant is selected from the group consisting of: sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, triethanolamine cocoamphoacetate, and mixtures thereof.

In an embodiment, the composition comprises a zwitterionic surfactant, wherein the zwitterionic surfactant is a derivative of an aliphatic quaternary ammonium, phosphonium, and sulfonium compound, in which the aliphatic radicals are straight or branched chain, and wherein one of the aliphatic substituents contains from about 8 to about 18 carbon atoms and one contains an anionic group such as carboxy, sulfonate, sulfate, phosphate or phosphonate. In an embodiment, the zwitterionic surfactant is selected from the group consisting of: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof. In an embodiment, the zwitterionic surfactant is selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

In an embodiment, the co-surfactant is selected from the group consisting of: zwitterionic surfactants, amphoteric surfactants, non-ionic surfactants, and mixtures thereof. In an embodiment, the surfactant is an anionic surfactant and the composition further comprises a co-surfactant, wherein the co-surfactant is selected from the group consisting of: zwitterionic surfactants, amphoteric surfactants, non-ionic surfactants, and mixtures thereof. In an embodiment, the co-surfactant is a non-ionic surfactant selected from the group consisting of: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, and mixtures thereof. In an embodiment, the co-surfactant is a zwitterionic surfactant, wherein the zwitterionic surfactant is selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

Associative Thickeners

Another class of thickeners along with conventional thickeners is associative thickeners. This class contains polymers which modify the rheology of a fluid through associative interactions between polymer chains, the dispersed phase, and the medium. Unlike conventional thickeners, associative thickeners are often times lower molecular weight polymers containing both hydrophilic and hydrophobic regions. The hydrophobic regions are then able to associate with the hydrophobic moieties while the hydrophilic regions are able to associate with the hydrophilic moieties. This can lead to a network formed within a mixture leading to high viscosities and unique rheological properties.

There are various types of associative thickening polymers, such as hydrophobically modified hydroxyethyl celluloses, hydrophobically modified polypolyacrylates, hydrophobically modified polyacrylic acids, hydrophobically modified polyacrylamides, and hydrophobically modified polyethers.

The class of hydrophobically-modified polyethers include numerous members such as PEG-120-methylglucose dioleate, PEG-N(40 or 60) sorbitan tetraoleate, PEG-150 pentaerythrityl tetrastearate, PEG-55 propylene glycol oleate and PEG-150 distearate. Typically these materials have a hydrophobe, non-limiting examples include cetyl, stearyl, oleayl and combinations thereof, and a hydrophilic portion of repeating ethylene oxide groups with repeat units from 10-300, in an embodiment, from 30-200, and in a further embodiment from 40-150.

The level of associative thickeners, such as PEG-150 distearate, is from about 0.5% to about 3.0%, from about 0.8% to about 2.5%, and from about 1% to about 2%, by weight of the shampoo composition.

Polyols

Polyols are a component of the present invention. In an embodiment of the present invention, a nonlimiting example of a polyol is glycerin. Glycerin is a colorless, odorless, viscous liquid that is very common for use in personal care applications and pharmaceutical formulations. Glycerin contains three hydroxyl groups that are responsible for its solubility in water and its humectant nature. Glycerin is well known as hair and skin benefit agent in personal care applications. This material can penetrate into a human hair to provide conditioning and softness via plasticization of the hair fiber while maintaining a very clean surface feel. Glycerin has been observed to clean more hydrophobic soil components (ie. sebum) than water.

The levels of Glycerin paired with PEG-150 distearate range from about 1.0% to about 10%, from about 2% to about 8% and from about 3.0% to about 6.0% by weight of the shampoo composition.

In another embodiment of the present invention, other polyols may be used. Nonlimiting examples include propylene glycol, sugar polyols such as sorbitol, aloe vera gel and honey.

Silicones

The conditioning agent of the compositions of the present invention can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference. The silicone conditioning agents for use in the compositions of the present invention can have a viscosity, as measured at 25° C., from about 20 to about 2,000,000 centistokes ("csk"), from about 1,000 to about 1,800,000 csk, from about 50,000 to about 1,500,000 csk, and/or from about 100,000 to about 1,500,000 csk.

The dispersed silicone conditioning agent particles typically have a volume average particle diameter ranging from about 0.01 micrometer to about 50 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, and/or from about 20 micrometer to about 50 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use in the embodiments of the present invention include, but are not limited to, emulsions of insoluble polysiloxanes prepared in accordance with the descriptions provided in U.S. Pat. No. 4,476,282 and U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micron. The average particle size may be within the range from about 40 nm to about 5 micron, from about 50 nm to about 1 micron, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscosimeter with spindle 6 at 2.5 rpm. The silicone emulsion may further include an additional emulsifier together with the anionic surfactant, Other classes of silicones suitable for use in compositions of the present invention include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

Organic Conditioning Materials

The conditioning agent of the shampoo compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Emulsifiers

A variety of anionic and nonionic emulsifiers can be used in the shampoo composition of the present invention. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

Chelating Agents

The shampoo composition can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term include alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440.

Levels of the EDDS chelant in the shampoo compositions can be as low as about 0.01 wt % or even as high as about 10 wt %, but above the higher level (i.e., 10 wt %) formulation and/or human safety concerns may arise. In an embodiment, the level of the EDDS chelant may be at least about 0.05 wt %, at least about 0.1 wt %, at least about 0.25 wt %, at least about 0.5 wt %, at least about 1 wt %, or at least about 2 wt % by weight of the shampoo composition. Levels above about 4 wt % can be used but may not result in additional benefit.

Gel Network

The shampoo composition may also comprise fatty alcohol gel networks. These gel networks are formed by combining fatty alcohols and surfactants in the ratio of from about 1:1 to about 40:1, from about 2:1 to about 20:1, and/or from about 3:1 to about 10:1. The formation of a gel network involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel network. The gel network contributes a stabilizing benefit to cosmetic creams and hair conditioners. In addition, they deliver conditioned feel benefits for hair conditioners.

The fatty alcohol can be included in the fatty alcohol gel network at a level by weight of from about 0.05 wt % to about 14 wt %. For example, the fatty alcohol may be present in an amount ranging from about 1 wt % to about 10 wt %, and/or from about 6 wt % to about 8 wt %.

The fatty alcohols useful herein include those having from about 10 to about 40 carbon atoms, from about 12 to about 22 carbon atoms, from about 16 to about 22 carbon atoms, and/or about 16 to about 18 carbon atoms. These fatty alcohols can be straight or branched chain alcohols and can be saturated or unsaturated. Nonlimiting examples of fatty alcohols include cetyl alcohol, stearyl alcohol, behenyl alcohol, and mixtures thereof. Mixtures of cetyl and stearyl alcohol in a ratio of from about 20:80 to about 80:20 are suitable.

Gel network preparation: A vessel is charged with water and the water is heated to about 74° C. Cetyl alcohol, stearyl alcohol, and SLES surfactant are added to the heated water. After incorporation, the resulting mixture is passed through a heat exchanger where the mixture is cooled to about 35° C. Upon cooling, the fatty alcohols and surfactant crystallized to form a crystalline gel network. Table 1 provides the components and their respective amounts for an example gel network composition.

TABLE 1

| Gel network components | |
|---|---|
| Ingredient | Wt. % |
| Water | 78.27% |
| Cetyl Alcohol | 4.18% |
| Stearyl Alcohol | 7.52% |
| Sodium laureth-3 sulfate (28% Active) | 10.00% |
| 5-Chloro-2-methyl-4-isothiazolin-3-one, Kathon CG | 0.03% |

In accordance with embodiments of the present invention, the personal care composition may further comprise one or more benefit agents. Exemplary benefit agents include, but are not limited to, particles, colorants, perfume microcapsules, gel networks, and other insoluble skin or hair conditioning agents such as skin silicones, natural oils such as sun flower oil or castor oil. In an embodiment, the benefit agent is selected from the group consisting of: particles; colorants; perfume microcapsules; gel networks; other insoluble skin or hair conditioning agents such as skin silicones, natural oils such as sun flower oil or castor oil; and mixtures thereof.

The composition forms coacervate particles upon dilution of the composition with water. The percentage of coacervate particles with a floc size of greater than about 20 micron is from about 1% to about 60%. In an embodiment, the percentage of coacervate particles with a floc size of greater than about 20 micron is from about 1% to about 50%, or from about 1% to about 40%, or from about 1% to about 30%, or from about 5% to about 20% from about 5% to about 15%. The floc size is measured after diluting the composition 1:50 dilution with water.

The floc size may be measured using a Lasentec FBRM Method: In a suitable mixing vessel create a 1:9 dilution of composition in distilled water at ambient temperature and mix for 5 min at 250 rpm. Using a peristaltic pump transfer ambient distilled water into the mixing vessel at a rate of 100 g/min resulting in a final dilution of 1:50 parts composition to distilled water. After a 10 min equilibration period a Lasentec Focused Beam Reflectance Method (FBRM) [model S400A available from Mettler Toledo Corp] may be used to determine floc size and amount as measured by chord length and particle counts/sec (counts per sec).

In an embodiment of the method, a mean consumer acceptance rating, on a scale of 20 to 100, of 20 is poor, or 40 is fair, or 60 is good, 80 is very good, and 100 is excellent is achieved. In order to obtain mean consumer acceptance rating values, compositions are evaluated by consumer panels ranging in size from 10 to 400, for example 16 to 310 people. Panelists are asked to use the composition as their only shampoo over a period of time ranging from 3 days to 4 weeks. After use, the panelists are asked to rate different attributes of the composition and its usage experience on a 5 point scale. For the purpose of numerical analysis, the answers are converted to a 100 point scale and the mean consumer acceptance rating calculated.

EXAMPLES

The following examples illustrate the present invention. The exemplified compositions can be prepared by conventional formulation and mixing techniques. It will be appreciated that other modifications of the present invention within the skill of those in the hair care formulation art can be undertaken without departing from the spirit and scope of this invention. All parts, percentages, and ratios herein are by weight unless otherwise specified. Some components may come from suppliers as dilute solutions. The levels given reflect the weight percent of the active material, unless otherwise specified.

Non-limiting Examples 1-25 are embodiments of the present invention.

| COMPOSITION | EXAMPLE | | | | | | | | | | |
| --- | --- | --- | --- | --- | --- | --- | --- | --- | --- | --- | --- |
| | 1 | 2 | 3 | 4 | 5 | 6 | 7 | 8 | 9 | 10 | 11 |
| Sodium Laureth Sulfate (SLE$_3$S) (1) | | | | | | | | | | | |
| Sodium Laureth Sulfate (SLE$_1$S) (2) | 11.5 | 11.5 | 11.5 | 11.5 | 11.5 | 11.5 | 11.5 | 11.5 | 11.5 | 11.5 | 11.5 |
| Glycerin (3) | 3 | 3 | 3 | 5 | 6 | 3 | 3 | 3 | 3 | 5 | 3 |
| Sodium Lauryl Sulfate (SLS) (4) | 1.5 | 1.5 | 1.5 | 1.5 | 1.5 | 1.5 | 1.5 | 1.5 | 1.5 | 1.5 | |
| Lauryl Hydroxysultaine (5) | 1 | 1 | 1 | 1 | 1.5 | 1 | | | | | |
| Cocamidopropyl Betaine (6) | | | | | | | | 1 | 1 | 1 | 1 |
| Cocamide MEA (7) | 1 | 1 | 1 | 1 | 1.5 | 1 | 1 | 1 | 1 | 1 | 1 |
| Glycol Distearate (8) | 1.5 | 1.5 | 1.5 | 1.5 | 1.5 | 1.5 | 1.5 | 1.5 | 1.5 | 1.5 | 1.5 |
| PEG-150 Distearate (9) | 1.5 | 1.5 | 1.5 | 1.5 | 1.5 | 1.5 | 1.5 | 1.5 | 1.5 | 1.5 | 1.5 |
| Zinc Pyrithione (10) | 1 | 1 | 1 | 1 | 1 | 1 | 1 | 1 | 1 | 1 | 1 |
| Zinc Carbonate (11) | 1.61 | 1.61 | 1.61 | 1.61 | 1.61 | 1.61 | 1.61 | 1.61 | 1.61 | 1.61 | 1.61 |
| Fragrance | 0.7 | 0.7 | 0.7 | 0.7 | 0.7 | 0.7 | 0.7 | 0.7 | 0.7 | 0.7 | 0.7 |
| Guar Hyrdroxypropyltrimonium Chloride (LMW) (12) | | | | | | | | | | | |
| Guar Hyrdroxypropyltrimonium Chloride (HMW) (13) | | | | | | 0.4 | | | | | |
| Guar Hyrdroxypropyltrimonium Chloride/ trimethylammonio propyl-methacrylamide/acrylamide copolymer (14) | 0.25 | 0.4 | 0.6 | 0.6 | 0.6 | — | 0.25 | 0.4 | 0.6 | 0.6 | 0.6 |
| Stearyl Alcohol (15) | | | | | | | | | | | |
| Cetyl Alcohol (16) | | | | | | | | | | | |
| Hydrochloric acid | QS | QS | QS | QS | QS | QS | QS | QS | QS | QS | QS |
| Preservative (17) | 0.05 | 0.05 | 0.05 | 0.05 | 0.05 | 0.05 | 0.05 | 0.05 | 0.05 | 0.05 | 0.05 |
| Sodium Chloride | QS | QS | QS | QS | QS | QS | QS | QS | QS | QS | QS |
| Sodium Xylene Sulfonate | QS | QS | 0.05 | QS | QS | QS | QS | QS | QS | QS | QS |
| Sodium Benzoate | 0.27 | 0.27 | 0.27 | 0.27 | 0.27 | 0.27 | 0.27 | 0.27 | 0.27 | 0.27 | 0.27 |
| Dimethicone (18) Dimethiconol (19) | 2 | 2 | 2 | 2 | 2 | 2 | 2 | 2 | 2 | 2 | 2 |
| Water and Minors (QS to 100%) | QS | QS | QS | QS | QS | QS | QS | QS | QS | QS | QS |

| COMPOSITION | EXAMPLE | | | | | | | | | | |
| --- | --- | --- | --- | --- | --- | --- | --- | --- | --- | --- | --- |
| | 12 | 13 | 14 | 15 | 16 | 17 | 18 | 19 | 20 | 21 | 22 |
| Sodium Laureth Sulfate (SLE$_3$S) (1) | | | | | | | | 6 | | | |
| Sodium Laureth Sulfate (SLE$_1$S) (2) | 11.5 | 12 | 12 | 12 | 12 | 12 | 12 | | 11.5 | 11.5 | 11.5 |
| Glycerin (3) | 6 | 3 | 3 | 3 | 5 | 6 | 6 | | | | 3 |
| Sodium Lauryl Sulfate (SLS) (4) | 1.5 | | | | | | | 7 | 1.5 | 1.5 | 1.5 |
| Lauryl Hydroxysultaine (5) | | 1 | 1 | 1 | 1 | 1 | 1.5 | | 1 | 1 | 1 |
| Cocamidopropyl Betaine (6) | 1.5 | | | | | | | 1 | | | |
| Cocamide MEA (7) | 1.5 | 1 | 1 | 1 | 1 | 1 | 1.5 | | 1 | 1 | 1 |
| Glycol Distearate (8) | 1.5 | 1.5 | 1.5 | 1.5 | 1.5 | 1.5 | 1.5 | 1.5 | 1.5 | 1.5 | 1.5 |
| PEG-150 Distearate (9) | 1.5 | 1.5 | 1.5 | 1.5 | 1.5 | 1.5 | 1.5 | | | | 1.5 |
| Zinc Pyrithione (10) | 1 | 1 | 1 | 1 | 1 | 1 | 1 | 1 | 1 | 1 | 1 |
| Zinc Carbonate (11) | 1.61 | 1.61 | 1.61 | 1.61 | 1.61 | 1.61 | 1.61 | 1.16 | 1.61 | 1.61 | 1.61 |
| Fragrance | 0.7 | 0.7 | 0.7 | 0.7 | 0.7 | 0.7 | 0.7 | | 0.7 | 0.7 | 0.7 |
| Guar | | | | | | | | 0.23 | | | |

-continued

| | | | | | | | | | | | |
|---|---|---|---|---|---|---|---|---|---|---|---|
| Hyrdroxypropyltri-monium Chloride (LMW) (12) | | | | | | | | | | | |
| Guar Hyrdroxypropyltri-monium Chloride (HMW) (13) | | | | | | | | | 0.4 | | |
| Guar Hyrdroxypropyltri-monium Chloride/ trimethylammonio propyl-methacrylamide/acryl-amide copolymer (14) | 0.6 | 0.25 | 0.4 | 0.6 | 0.6 | 0.6 | 0.6 | | 0.6 | — | 0.6 |
| Stearyl Alcohol (15) | | | | | | | | | | | 1.29 |
| Cetyl Alcohol (16) | | | | | | | | | | | 0.71 |
| Hydrochloric acid | QS | QS | QS | QS | QS | QS | QS | QS | QS | QS | QS |
| Preservative (17) | 0.05 | 0.05 | 0.05 | 0.05 | 0.05 | 0.05 | 0.05 | 0.05 | 0.05 | 0.05 | 0.05 |
| Sodium Chloride | QS | QS | QS | QS | QS | QS | QS | QS | QS | QS | QS |
| Sodium Xylene Sulfonate | QS | QS | QS | QS | QS | QS | QS | QS | QS | QS | QS |
| Sodium Benzoate | 0.27 | 0.27 | 0.27 | 0.27 | 0.27 | 0.27 | 0.27 | 0.27 | 0.27 | 0.27 | 0.27 |
| Dimethicone (18) | | | | | | | | 0.8 | | | |
| Dimethiconol (19) | 2 | 2 | 2 | 2 | 2 | 2 | 2 | | 2 | 1 | 2 |
| Water and Minors (QS to 100%) | QS | QS | QS | QS | QS | QS | QS | QS | QS | QS | QS |

(1) Sodium Laureth-3 Sulfate from the Stepan Company
(2) Sodium Laureth-1 Sulfate from the Stepan Company
(3) Glycerin from Procter & Gamble
(4) Sodium Lauryl Sulfate from Stepan Company
(5) Mackam LHS from Rhodia
(6) Amphosol HCA from Stepan Company
(7) Ninol COMF from Stepan Company
(8) EGDS from Golschmidt Chemical Company
(9) Lipopeg 6000 Distearate Lipo Chemical Company
(10) ZPT from Arch Chemical
(11) Zinc Carbonate from Bruggeman Group
(12) Jaguar C500 from Rhodia with a M. Wt of 500,000 g/mol and charge density of 0.8 meq/g
(13) N Hance 3196 from Aqualon 1,700,000 g/mol and charge density of 0.7 meq/g
(14) A blend from Ashland, which is a blend of 95:5 guar hydroxypropyltrimonium chloride (M. Wt 500,000 g/mol; charge density 1.1 meq/g to AM/APTAC (M. Wt 1,100,000 g/mol; charge density 1.8 meq/g
(15) CO 1895 from Procter & Gamble
(16) CO 1695 from Procter & Gamble
(17) Kathon CG from Akzo Nobel
(18) Viscasil 330M from Momentive Performance Materials with a viscosity of 330,000 cSt (centistokes).
(19) BELSIL DM from Wacker Silicones
(20) Tryhydroxystearin (Hydrogenated Castor Oil) from Elementis
(21) N-Hance BF-17 from Ashland (850,000 g/mol and charge density of 1.4 meq/g)
(22) Poly(Diallyl Dimethyl Ammonium Chloride) from Rhodia
(23) Ethylene Diamine Tetra Acetic Acid (Dissolvine 220-S) from Akzo Nobel (Herkenbosch NL)
(24) Citric Acid Anhydrous from Archer Daniels Midland (Southport US) - used to adjust product pH from 4-7

Rheology Method Used:

In the continuous ramp flow experiment, the neat shampoo is loaded between a cone and plate with a radius of 40 mm and a cone angle of 2 degrees, on a conventional rheometer TA AR2000. The product is removed from a shampoo container imparting as little shear as possible. Product is applied to the steel plate and allowed to relax for 60 seconds. The top plate is lowered at a constant linear velocity as the gap decreased. During this process the normal force exerted by the sample on the lower plate is measured by the rheometer. Final gap height is measured at 59 microns. Shear stress (Pa) is applied from 6.0 E-3 to 800 Pa with samples taken at 30 points per decade at a temperature of 25° C. Data is analyzed via software TA Rheology Advantage Data Analysis V5.7.0. The data output is viscosity (Pa·s) versus shear rate (1/s). FIG. 1 shows this data plotted as symbols and the solid line is the model fit using the Carreau model analysis. The Carreau model analysis uses the Carreau Model Calculation where the input variables are:

$\eta$=Viscosity at each shear rate
$\gamma$=Shear rate (1/s)
and the output parameters determined by the Carreau model are:
$\eta_{infinity}$=Viscosity at high shear rate>1500 1/s
$\eta_{zero\ shear}$=Viscosity at very low shear rate<0.2 1/s
$\lambda$=Consistency (value in seconds where the viscosity vs. shear rate curve has an inflection and begins to shear thin)
N=Rate index (slope of shear thinning portion of viscosity vs. shear rate curve)
Carreau Model Calculation $$\frac{\eta - \eta_{infinity}}{\eta_{zero\ shear} - \eta_{infinity}} = [1 + (\lambda\gamma)^2]^{\frac{(N-1)}{2}}$$

The Carreau model analysis can be done using the TA Rheology software V.5.7.0 or any curve fitting/regression analysis available to one skilled in the art. Using the Carreau Model analysis data parameters are demonstrated for compositions in Example table and are shown in Table 2. Compositions 3 and 4 and 6 demonstrate results from formulations that contain PEG-150 distearate and glycerin. Compositions 3 and 4 demonstrate similar rate index (N) values (0.45 and 0.42 respectively) as indicated by the rate indexes in Table 2. Composition 6 exhibits the most shallow rate index (N) noted by a low value of 0.28.

Shampoos compositions 19, 20, and 21 which do not contain PEG-150 distearate and glycerin are observed to have much steeper rate index (N) as indicated by values of 0.97, 0.73, and 0.58 respectively. Composition 20 which is most similar to composition 3, with the exception of PEG-150 distearate and Glycerin, demonstrates a similar consistency value (λ) to composition 3 (0.09 vs. 0.15) but rate index value (N) is much higher (0.73 vs. a 0.45). Composition 19 demonstrates a low consistency (λ) and high rate index (N) (0.09 (s) and 0.97 respectively and shown in FIG. 1.

Composition 21 is most similar to Composition 6 with the exception of PEG-150 distearate and Glycerin, Composition 21 shows a consistency value (λ) lower than composition 6 (1.06 vs. 4.53). The rate index value is larger for composition 21 vs. composition 6 (0.58 vs. 0.28)

and glycerin presence represented by the label x. Column 3. indicates data for consumer preference of lather amount. Column 4. indicates consumer preference for ease to rinse. Column 5. indicates consumer preference for smooth when wet. Column 6 identifies consumer preference for overall conditioning. Column 7 identifies consumer preference for achieving the look a consumer wants. Column 8 identifies consumer preference for leaving hair moisturized. Column 9. represents zero rate viscosity (Pa·s) determined via Carreau model analysis. Column 10. identifies infinite rate viscosity (Pa·s) determined via the Carreau model analysis. Column 11. identifies consistency values (λ) determined via Carreau model analysis. Column 12. identifies rate index values (N) determined via Carreau model analysis. Column 13 identifies % coacervate particles with floc size> than 20 microns obtained via the Lasentec particle size experimentation. Column 14. identifies in vivo scalp zinc pyrithione (ZPT) deposition data results.

Consumer Data Description

Column 1 Identifies Compositions Referred to in the Example Table 2.

Column 2 of Table 2. identifies PEG-150 distearate/Glycerin containing compositions labeled with an "x" when said material is present. Consumer data (Columns 3, 4, 5, 6, 7, 8) represents a consumer population of women considered non-antidandruff users for composition 3 (n=19), composi-

TABLE 2

| Column 1. | Column 2. | Column 3. | Column 4. | Column 5. | Column 6. | Column 7. | Column 8. |
|---|---|---|---|---|---|---|---|
| | | Non AD Women consumer | Non AD Women consumer | Non AD Women consumer | Non AD Women consumer | Non AD Women consumer | Non AD Women consumer |
| Composition | PEG150DS/ Glycerin | Lather amount | Easy to rinse | Smooth when wet | Overall Conditioning | Achieving the look I want | Leaving hair moisturized |
| 3 (n = 19) | x | /////////////// | /////////////// | /////////////// | xxxxxxxxxxxx | xxxxxxxxxxxx | /////////////// |
| 4 | x | — | — | — | — | — | — |
| 6 | (n = 21) | xxxxxxxxxxxx | xxxxxxxxxxxx | /////////////// | /////////////// | /////////////// | /////////////// |
| 21(n = 26) | — | ********** | ********** | ********** | ********** | ********** | ********** |
| 19 | — | — | — | — | — | — | — |
| 20 | — | — | — | — | — | — | — |

| Column 1. | Column 2. | Column 9. | Column 10. | Column 11. | Column 12. | Column 13. | Column 14. |
|---|---|---|---|---|---|---|---|
| | | | | Between (0.01-0.2) | (r < 0.6) | % Coacervate particles with floc size > 20 microns | in vivo ZPT Scalp Deposition |
| Composition | PEG150DS/ Glycerin | Zero rate viscosity (Pa.s) | Infinite rate viscosity (Pa.s) | consistency λ(s) | rate index (N) | microns | ug/cm$^2$ |
| 3 (n = 19) | x | 17.5 | 1.05E-05 | 0.15 | 0.45 | 24.7 | (n = 25) * 3.2 |
| 4 | x | 33.8 | 7.30E-07 | 0.19 | 0.42 | — | — |
| 6 | (n = 21) | 42.6 | 7.17E-07 | 4.53 | 0.28 | 45.6 | — |
| 21(n = 26) | — | 35.1 | 1.35E-06 | 1.06 | 0.58 | 70.6 | — |
| 19 | — | 14.5 | 3.89E-07 | 0.09 | 0.97 | 16.4 | (n = 25) 1.7 |
| 20 | — | 12.2 | 4.11E-07 | 0.12 | 0.73 | 27.8 | — |

| Key | Consumer Response |
|---|---|
| /////////////// | Strong positive accpetance |
| xxxxxxxxxxxx | Moderate acceptance |
| ********** | Poor acceptance |

Table 2: Column 1. Identifies compositions. Panelists are asked to use the composition as their only shampoo over a period of 2 weeks. Column 2. indicates PEG-150 distearate tion 6 (n=21), and composition 21 (n=26). Consumer data indicates that composition 3 is the strongest accepted composition for "lather amount" (Column 3) when compared to composition 6 showing moderate acceptance and composition 21 exhibiting poor acceptance. Consumer acceptance for "easy to rinse" (Column 4) indicates that composition 3 has the strongest acceptance with composition 6 exhibiting moderate acceptance and composition 21 exhibiting the poorest acceptance. Consumer data indicates "smooth when wet" (Column 5) acceptance is strongest for both composition 3 and 6 with composition 21 exhibiting the poorest acceptance. Consumer data for "overall conditioning" (Column 6) indicates that composition 6 is strongly accepted, composition 3 is moderately accepted, and composition 21 is poorly accepted. Consumer data for "achieving the look I want" indicates that composition 6 is strongly accepted, and composition 3 is moderately accepted while composition 21 is poorly accepted. Consumer data for "leaving hair moisturized" indicates that both composition 3 and 6 are strongly accepted vs. composition 21 which is poorly accepted.

Discussion:

According to Table 2. (Columns 1 thru 8) compositions 3, 6 and 21 have consumer data which identifies non antidandruff user consumer responses to questions on lather amount, easy to rinse, smooth when wet, overall conditioning, achieving the look wanted, and leaving hair moisturized. It is observed that both compositions 3 and 6, which contain PEG-150 distearate and glycerin, have positive acceptance across all consumer questions vs. compositions 21 which contains no PEG-150 distearate and glycerin and has observed poor consumer acceptance.

Rheology data which has been identified in columns 9 thru 12 show values determined from Carreau analysis. These values include zero rate viscosity ($\eta_{zero\ shear}$), infinite viscosity ($\eta_{infinity}$), consistency ($\lambda$) and rate index (N).

Compositions which contain consumer data (compositions 3, 6, and 21) show data difference mostly in the consistency ($\lambda$) measurement. It is observed that compositions 3 and 6 have very different consistency values ($\lambda$) 0.15 s and 4.53 s respectively. The rate index values (N) for compositions 3 and 6 are comparable 0.43(N) vs. 0.28(N) respectively. Composition 21, a poor accepted consumer product, also has a higher observed consistency value ($\lambda$) vs. the positive consumer accepted composition 3, (1.06 s vs. 0.15 s respectively) but is not as high as composition 6 (4.53 s).

When evaluating consumer data consistency ($\lambda$) and % coacervate particles with floc size> than 20 microns need to be considered to provide a complete picture for consumer acceptance and anti-dandruff efficacy performance. Column 13 shows lasentec data values identified as the % coacervate particles with a floc size of greater than 20 microns. Composition 3 has the lowest observed floc size measured at (24.7 microns) vs. composition 6 at (45.6 microns) and composition 21 at (70.6 microns). It is understood that compositions with large coacervate floc 40 micron or greater % coacervate particles with floc size greater than 20 microns will yield poor efficacy and hair feel. In vivo zinc pyrithione scalp deposition for composition 3 indicates high zinc pyrithione deposition quantity (3.2 ug/cm2) when compared with composition 19 (1.7 ug/cm2).

In the present invention, the yield consistency value may be in the range of from about 0.001 s to 0.9 s, and in a further embodiment may be from about 0.01 to about 0.45 s, and in an embodiment of the present invention, the yield consistency value may be from about 0.1 s to about 0.2 s.

Rate index values (N) are also used to establish rheological differences between compositions. Differences can be observed when comparing Composition 3 (0.45(N)) to Composition 20 (0.73(N)) which are the same compositionally with exception of PEG-150 distearate/glycerin present in composition 3 and no PEG-150 distearate/glycerin in composition 20. Higher rate index values are interpreted as more shear thinning than lower rate index values. A high rate index value (0.97(N)) is also observed for composition 19 which also does not contain PEG-150 distearate/glycerin. A upper limit of about 0.6(N) rate index is set as a threshold by which compositions will be viewed by the consumer as more cosmetically acceptable. In the present invention, the rate index value (N) may be in the range of from about 0.01 to about 0.6, and in a further embodiment may be from about 0.1 to about 0.5.

It is therefore deduced that composition 3 containing PEG-150 distearate/glycerin which has observed positive consumer response and consistency value of 0.15 s with rate value of 0.45(N) and 24.71 micron floc % coacervate particles with floc size greater than 20 microns will achieve an antidandruff formulation that is consumer accepted by a non antidandruff user while maintaining antidandruff active deposition and coacervate floc size.

TABLE 3

Stats 90% confidence

| Composition | Shampoo Texture | Lather amount | Easy to lather | Smooth when wet | Overall Conditioning | Achieve look | Moisturerized |
|---|---|---|---|---|---|---|---|
| 3 (n = 300) | ///////////// | xxxxxxxx | ///////////// | xxxxxxxx | xxxxxxxx | xxxxxxxx | ******** |
| 6 (n = 300) | ///////////// | ///////////// | ///////////// | xxxxxxxx | xxxxxxxx | xxxxxxxx | ///////////// |
| 20 + 1% extra SLE1S (n = 300) | ******** | ******** | ******** | ******** | ******** | ******** | ******** |

| Key | Consumer Response |
|---|---|
| ///////////// | Sig Positive |
| xxxxxxxx | Directional Positive |
| ******** | Parity |

Table 3 identifies consumer response from a large scale antidandruff shampoo consumer evaluation (n=300/leg). Panelists are asked to use the composition as their only shampoo over a period of 4 weeks. These data are in support as further evidence that Rep populations of male and female consumers, whom are concerned with dandruff, prefer formulas (composition 3 and 6) with rheological modification via formulation variables such as PEG150 distearate and glycerin when compared to formulations that are void of those materials (composition 20+extra 1% SLE1S). Highlighted consumer responses are observed for shampoo texture, lather amount, easy to lather, smooth when wet, overall conditioning, achieve look, and moisturized. Significant positive responses are observed for composition 6 of shampoo texture, lather amount, easy to lather, and moisturized. Significant positive responses are also observed for composition 3 in texture of shampoo and easy to lather. Directionally positive response is observed for composition 3 vs. composition 20+extra 1% SLE1S for lather amount. Directional positive response for smooth when wet, overall conditioning, and achieve look are observed for composition 3 and composition 6 vs. composition 20+extra 1% SLE1S. Parity response is observed for composition 3 and composition 20+extra 1% SLE1S for moisturized.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A method of achieving improved composition rheology, cosmetic consumer acceptance and deposition comprising applying to hair a composition comprising
    a) from about 0.01% to about 2% of a cationic polymer;
    b) from about 0.5% to 3% of an associative thickener;
    c) from about 1.0% to 10.0% of a polyol;
    d) an anti-dandruff active wherein the anti-dandruff active is zinc pyrithione;
    e) a cosmetically acceptable carrier;
    f) a surfactant;
    wherein the composition comprises a zinc-containing layered material selected from the group consisting of basic zinc carbonate, zinc carbonate hydroxide, hydrozincite, zinc copper carbonate hydroxide, aurichalcite, copper zinc carbonate hydroxide, rosasite, phyllosilicate containing zinc ions, layered double hydroxide, hydroxy double salts, and mixtures thereof and wherein the composition comprises a yield consistency value of about 0.001s to 0.9s and having a rate index value of from about 0.01 to about 0.6 and a percentage of coacervate particles with a floc size of greater than about 20 microns is from about 1% to about 40%.

2. The method according to claim 1, wherein the polyol is glycerin.

3. The method according to claim 1 wherein the yield consistency value is from about 0.1s to about 0.2s.

4. The method according to claim 1 wherein the associative thickener is from about 1.0% to about 2.0%.

5. The method according to claim 1 wherein the associative thickener is selected from the group consisting of hydrophobically modified hydroxyethyl celluoloses, hydrophobically modified polypolyacrylates, hydrophobically modified polyacrylic acids, hydrophobically modified polyacrylamides, and hydrophobically modified polyethers and mixtures thereof.

6. The method according to claim 5 wherein the associative thickener is selected from the group consisting of PEG-120-methylglucose dioleate, PEGN(40 or 60) sorbitan tetraoleate, PEG-150 pentaerythrityl tetrastearate, PEG-55 propylene glycol oleate, PEG-150 distearate and mixtures thereof.

7. The method according to claim 5 wherein the associative thickener is PEG-150 distearate.

8. The method according to claim 1 wherein the cationic polymer is a cationic guar polymer.

9. The method according to claim 8 wherein the cationic guar polymer has a weight average molecular weight of less than about 3 million g/mol, and wherein the cationic guar polymer has a charge density of from about 0.1 meq/g to about 2.5 meq/g.

10. The method according to claim 9, wherein cationic guar polymer has a weight average molecular weight of from about 150 thousand to about 800 thousand g/mol.

11. The method according to claim 10, wherein cationic guar polymer has a weight average molecular weight of from about 200 thousand to about 700 thousand g/mol.

12. The method according to claim 1, wherein the on-scalp deposition of the zinc pyrithione is at least about 1 microgram/cm$^2$.

13. The method according to claim 1, wherein the cosmetically acceptable carrier is a cosmetically acceptable aqueous carrier and is present at a level of from about 20% to about 95%.

14. The method according to claim 1, wherein the composition comprises from about 0.01% to about 0.7% cationic polymer, by total weight of the composition.

15. The method according to claim 1, wherein the composition comprises a cationic copolymer.

16. The method according to claim 1, wherein the surfactant is an anionic surfactant.

17. The method according to claim 1, wherein the composition further comprises a co-surfactant, wherein the co-surfactant is selected from the group consisting of zwitterionic surfactants, amphoteric surfactants, non-ionic surfactants, and mixtures thereof.

* * * * *